United States Patent [19]

Hoffmann et al.

[11] 4,036,982

[45] July 19, 1977

[54] O-ALKYL-S-ALKYL-O-[2-CARBALKOXY-BENZOFURAN(3)YL]-THIONOTHIOL-PHOSPHORIC ACID ESTERS

[75] Inventors: Hellmut Hoffmann; Hans-Jochem Riebel, both of Wuppertal; Ingeborg Hammann, Cologne, all of Germany

[73] Assignee: Bayer Aktiengesellschaft, Leverkusen, Germany

[21] Appl. No.: 709,979

[22] Filed: July 30, 1976

[30] Foreign Application Priority Data

Aug. 16, 1975 Germany ............................. 2536502

[51] Int. Cl.² ...................... A01N 9/36; C07D 307/85
[52] U.S. Cl. ............................... 424/285; 260/346.2 R
[58] Field of Search .................. 260/346.2 R; 424/285

[56] References Cited

U.S. PATENT DOCUMENTS 2,749,272  6/1956  Buntin ...................... 260/346.2 R X Primary Examiner—Henry R. Jiles
Assistant Examiner—Bernard Dentz
Attorney, Agent, or Firm—Burgess, Dinklage & Sprung

[57] ABSTRACT

O-Alkyl-S-alkyl-O-[2-carbalkoxy-benzofuran(3)yl]-thionothiolphosphoric acid esters of the formula

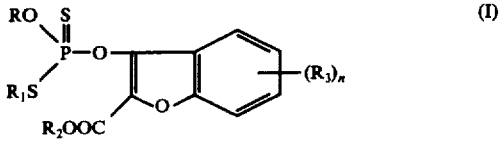

in which R, $R_1$ and $R_2$ each independently is alkyl with 1 to 6 carbon atoms, $R_3$ is halogen, or alkyl or alkoxy with 1 to 4 carbon atoms, and $n$ is an integer from 0 to 4, which possess insecticidal properties.

10 Claims, No Drawings

O-ALKYL-S-ALKYL-O-[2-CARBALKOXY-BENZOFURAN(3)YL]-THIONOTHIOL-PHOSPHORIC ACID ESTERS

The present invention relates to and has for its objects the provision of particular new substituted O-alkyl-S-alkyl-O-[2-carbalkoxy-benzofuran(3)yl]-thionothiolphosphoric acid esters which possess insecticidal properties, active compositions in the form of mixtures of such compounds with solid and liquid dispersible carrier vehicles, and methods for producing such compounds and for using such compounds in a new way especially for combating pests, e.g., insects, with other and further objects becoming apparent from a study of the within specification and accompanying examples.

It is already known from German published specification DAS No. 1,230,433 that benzothiophenethionophosphoric(phosphinic) acid esters, for example O,O-diethyl-O-[6-methoxy-benzothiophen(3)yl]-thionophosphoric acid ester (Compound A) and O-[6-methoxy-benzothiophen(3)yl]-thionodiethanephosphinic acid ester (Compound B) possess pesticidal, and above all insecticidal, properties.

The present invention provides benzofuranylthionothiolphosphoric acid esters of the general formula

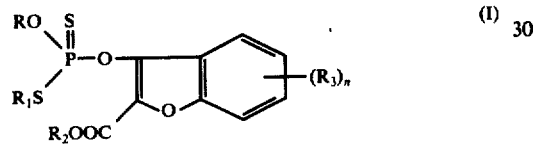

in which
R, $R_1$ and $R_2$ each independently is alkyl with 1 to 6 carbon atoms,
$R_3$ is halogen, or alkyl or alkoxy with 1 to 4 carbon atoms, and
n is an integer from 0 to 4.

Preferably, R represents straight-chain or branched alkyl with 1 to 3 carbon atoms, $R_1$ represents straight-chain or branched alkyl with 1 to 5 carbon atoms, $R_2$ represents straight-chain or branched alkyl with 1 to 4 carbon atoms, $R_3$ represents chlorine, methoxy, ethoxy, methyl or ethyl, and n represents 0, 1 or 2.

Surprisingly, the benzofuranylthionothiolphosphoric acid esters according to the invention exhibit a better insecticidal action than the corresponding benzothiophenethionophosphoric(phosphinic) acid esters of analogous structure and of the same type of action. The products according to the present invention thus represent a genuine enrichment of the art.

The invention also provides a process for the production of a benzofuranylthionothiolphosphoric acid ester of the formula (I) in which a thionothiolphosphoric acid diester halide of the formula

in which
R and $R_1$ have the above-mentioned meanings and Hal is halogen, preferably chlorine, is reacted with a 3-hydroxybenzofuran derivative of the formula

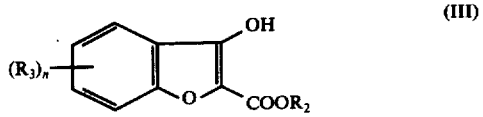

in which
$R_2$, $R_3$ and n have the above-mentioned meanings, optionally in the presence of an acid acceptor or in the form of an alkali metal salt or alkaline earth metal salt, and optionally in the presence of a solvent.

If, for example, O-n-propyl-S-sec.-butylthionothiolphosphoric acid diester chloride and 2-carbethoxy-5,6-dichloro-3-hydroxy-benzofurane are used as starting materials, the course of the reaction can be represented by the following formula scheme:

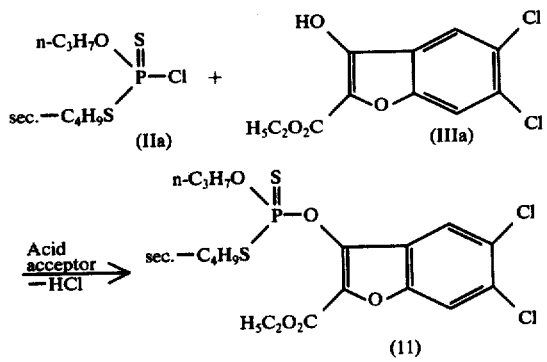

The thionothiolphosphoric acid diester halides (II) to be used as starting materials are known from U.S.S.R. Pat. No. 184,863 and can be prepared in accordance with generally known processes.

The following may be mentioned as individual examples of these halides: O,S-dimethyl-, O,S-diethyl-, O,S-di-n-propyl-, O,S-di-iso-propyl-, O-ethyl-S-n-propyl-, O-ethyl-S-iso-propyl-, O-ethyl-S-n-butyl-, O-ethyl-S-sec.-butyl-, O-n-propyl-S-ethyl, O-n-proyl-S-iso-propyl- and O-ethyl-S-n-pentylthionothiolphosphoric acid diester halide.

The 2-carbalkoxy-3-hydroxy-benzofuran derivatives (III) to be used as starting materials can be prepared in accordance with processes known from the literature, by cyclizing 2-carbalkoxyphenoxyacetic acid alkyl esters in the presence of a base.

The following may be mentioned as individual examples: 3-hydroxy-2-carbo-methoxy-, -ethoxy-, -n-propoxy-, -iso-propoxy-, -n-butoxy-, -iso-butoxy-, -sec.-butoxy- and -tert.-butoxy-benzofuran and the corresponding alkali metal salts and alkaline earth metal salts, as well as 5-chloro-, 5-methyl-, 5-ethyl-, 5-methoxy-, 5-ethoxy-, 7-chloro-, 7-methyl-, 7-ethyl-, 7-methoxy-, 7-ethoxy-, 5,7-dichloro-, 5,7-dimethyl-and 5,7-diethyl-3-hydroxy-2-carbo-methoxy-, -ethoxy-, -n-propoxy-, -iso-propoxy- and -butoxy-benzofuran and the corresponding alkali metal salts and alkaline earth metal salts.

The process according to the present invention is preferably carried out in the presence of a solvent, which term includes a mere diluent. Practically all inert organic solvents can be used for this purpose. These include, in particular, aliphatic and aromatic, optionally chlorinated, hydrocarbons, for example benzene, toluene, xylene, benzine, methylene chloride, chloroform, carbon tetrachloride and chlorobenzene; ethers, for example diethyl ether, dibutyl ether and dioxane; ketones, for example acetone, methyl ethyl ketone, methyl isopropyl ketone and methyl isobutyl ketone; and nitriles, for example acetonitrile and propionitrile.

All customary acid-binding agents can be used as acid acceptors. Alkali metal carbonates and alkali metal alcoholates, such as sodium carbonate and potassium carbonate, sodium methylate and ethylate and potassium methylate, ethylate and tert.-butylate, have proved particularly suitable, as have aliphatic, aromatic and heterocyclic amines, for example triethylamine, trimethylamine, dimethylaniline, dimethylbenzylamine and pyridine.

The reaction temperature can be varied within a substantial range. In general, the reaction is carried out at 0° to 120°C, preferably at 20° to 50°C.

In general, the reaction is allowed to take place under normal pressure.

In carrying out the process, the reactants are preferably employed in equimolar amounts. An excess of one or other reactant provides no significant advantages. In general, the reactants are brought together in one of the stated solvents, preferably at room temperature; thereafter the mixture may be stirred further, in most cases at an elevated temperature, for from one to several hours. The batch may be worked up in the usual manner by pouring the reaction mixture into an organic solvent, for example toluene, washing and drying the organic phase and distilling off the solvent.

The new compounds are obtained in the form of oils, some of which cannot be distilled without decomposition but can be freed from the last volatile constituents by so-called "slight distillation," that is to say prolonged heating under reduced pressure to moderately elevated temperatures, and they may be purified in this way. They are characterized by the refractive index.

As already mentioned, the benzofuranylthionothiolphosphoric acid esters according to the invention are distinguished by an excellent insecticidal activity. They are active against plant pests, hygiene pests and pests of stored products and combine a low phytotoxicity with a good action against both sucking and biting insects. They also exhibit relatively low mammalian toxicity.

For this reason, the compounds according to the invention can be employed successfully as pesticides in plant protection as well as in the hygiene field and in the field of protection of stored products.

To the sucking insects there belong, in the main, aphids (Aphididae) such as the green peach aphid (*Myzus persicae*), the bean aphid (*Doralis fabae*), the bird cherry aphid (*Rhopalosiphum padi*), the pea aphid (*Macrosiphum pisi*) and the potato aphid (*Macrosiphum solanifolii*), the currant gall aphid (*Cryptomyzus korschelti*), the rosy apple aphid (*Sappaphis mali*), the mealy plum aphid (*Hyalopterus arundinis*) and the cherry black-fly (*Myzus cerasi*); in addition, scales and mealybugs (Coccina), for example the oleander scale (*Aspidiotus hederae*) and the soft scale (*Lecanium hesperidum*) as well as the grape mealybug (*Pseudococcus maritimus*); thrisp (Thysanoptera), such as *Hercinothrips femoralis*, and bugs, for example the beet bug (*Piesma quadrata*), the red cotton bug (*Dysdercus intermedius*), the bed bug (*Cimex lectularius*), the assassin bug (*Rhodnius prolixus*) and Chagas' bug (*Triatoma infestans*) and, further, cicadas, such as *Euscelis bilobatus* and *Nephotettix bipunctatus*.

In the case of the biting insects, above all there should be mentioned butterfly and moth caterpillars (Lepidoptera) such as the diamond-back moth (*Plutella maculipennis*), the gypsy moth (*Lymantria dispar*), the brown-tail moth (*Euproctis chrysorrhoea*) and tent caterpillar (*Malacosoma neustria*); further, the cabbage moth (*Mamestra brassicae*) and the cutworm (*Agrotis segetum*), the large white butterfly (*Pieris brassicae*), the small winter moth (*Cheimatobia brumata*), the green oak tortrix moth (*Tortrix viridana*), the fall armyworm (*Laphygma frugiperda*) and cotton worm (*Prodenia litura*), the ermine moth (*Hyponomeuta padella*), the Mediterranean flour moth (*Ephestia Kühniella*) and greater wax moth (*Galleria mellonella*).

Also to be classed with the biting insects are beetles (Coleoptera), for example the granary weevil (*Sitophilus granarius* = *Calandra granaria*), the Colorado beetle (*Leptinotarsa decemlineata*), the dock beetle (*Gastrophysa viridula*), the mustard beetle (*Phaedon cochleariae*), the blossom beetle (*Meligethes aeneus*), the raspberry beetle (*Byturus tomentosus*), the bean weevil (Bruchidius = *Acanthoscelides obtectus*), the leather beetle (*Dermestes frischi*), the khapra beetle (*Trogederma granarium*), the flour beetle (*Tribolium castaneum*), the northern corn billbug (Calandra or *Sitophilus zeamais*), the drugstore beetle (*Stegobium paniceum*), the yellow mealworm (*Tenebrio molitor*) and the saw-toothed grain beetle (*Oryzaephilus surinamensis*), and also species living in the soil, for example wireworms (*Agriotes* spec.) and larvae of the cockchafer (*Melolontha melolontha*); cockroaches, such as the German cockroach (*Blattella germanica*), American cockroach (*Periplaneta americana*), Madeira cockroach (Leucophaea or *Rhyparobia maderae*), oriental cockroach (*Blatta orientalis*), the giant cockroach (*Blaberus giganteus*) and the black giant cockroach (*Blaberus fuscus*) as well as *Henschoutedenia flexivitta;* further, Orthoptera, for example the house cricket (*Gryllus domesticus*); termites such as the eastern subterranean termite (*Reticulitermes flavipes*) and Hymenoptera such as ants, for example the garden ant (*Lasius niger*).

The Diptera comprise essentially the flies, such as the vinegar fly (*Drosophila melanogaster*), the Mediterranean fruit fly (*Ceratitis capitata*), the house fly (*Musca domestica*), the little house fly (*Fannia canicularis*), the black blow fly (*Phormia regina*) and bluebottle fly (*Calliphora erythrocephala*) as well as the stable fly (*Stomoxys calcitrans*); further, gnats, for example mosquitoes such as the yellow fever mosquito (*Aëdes aegypti*), the northern house mosquito (*Culex pipiens*) and the malaria mosquito (*Anopheles stephensi*).

When applied against hygiene pests and pests of stored products, particularly flies and mosquitoes, the process products are also distinguished by an outstanding residual activity on wood and clay, as well as a good stability to alkali on limed substrates.

The active compounds according to the instant invention can be utilized, if desired, in the form of the usual formulations or compositions with conventional inert (i.e., plant compatible or herbicidally inert) pesticide diluents or extenders, i.e., diluents, carriers or extenders of the type usable in conventional pesticide formulations or compositions, e.g., conventional pesticide dispersible carrier vehicles such as gases, solutions, emulsions, suspensions, emulsifiable concentrates, spray powders, pastes, soluble powders, dusting agents, granules, etc. These are prepared in known manner, for instance by extending the active compounds with conventional pesticide dispersible liquid diluent carriers and/or dispersible solid carriers optionally with the use of carrier vehicle assistants, e.g., conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as Freon; inert dispersible liquid diluent carriers, including inert organic solvents, such as aromatic hydrocarbons (e.g., benzene, toluene, xylene, alkyl naphthalenes, etc.) halogenated, especially chlorinated, aromatic hydrocarbons (e.g. chlorobenzenes, etc.), cycloalkanes, (e.g., cyclohexane, etc.), paraffins (e.g., petroleum or mineral oil fractions), chlorinated aliphatic hydrocarbons (e.g., methylene chloride, chloroethylenes, etc.), alcohols (e.g., methanol, ethanol, propanol, butanol, glycol, etc.) as well as ethers and esters thereof (e.g., glycol monomethyl ether, etc.), amines (e.g., ethanolamine, etc.), amides (e.g., dimethyl formamide, etc.), sulfoxides (e.g., dimethyl sulfoxide, etc.), acetonitrile, ketones (e.g., acetone, methyl ethyl ketone, methyl isobutyl ketone, cyclohexanone, etc.), and/or water; as well as inert dispersible finely divided solid carriers, such as ground natural minerals (e.g., kaolins, clays, alumina, silica, chalk, i.e., calcium carbonate, talc, attapulgite, montmorillonite, kieselguhr, etc.) and ground synthetic minerals (e.g., highly dispersed silicic acid, silicates, e.g., alkali silicates, etc.); whereas the following may be chiefly considered for use as conventional carrier vehicle assistants, e.g., surface-active agents, for this purpose: emulsifying agents, such as non-ionic and/or anionic emulsifying agents (e.g., polyethylene oxide esters of fatty acids, polyethylene oxide ethers of fatty alcohols, alkyl sulfates, alkyl sulfonates, aryl sulfonates, albumin hydrolyzates, etc., and especially alkyl arylpolyglycol ethers, magnesium stearate, sodium oleate, etc.); and/or dispersing agents, such as lignin, sulfite waste liquors, methyl cellulose, etc.

Such active compounds may be employed alone or in the form of mixtures with one another and/or with such solid and/or liquid dispersible carrier vehicles and/or with other known compatible active agents, especially plant protection agents, such as other insecticides, or acaricides, nematocides, fungicides, bactericides, rodenticides, herbicides, fertilizers, growth-regulating agents, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1-95% by weight, and preferably 0.5-90% by weight, of the mixture, whereas carrier composition mixtures suitable for direct application or field application generally contemplate those in which the active compound is present in an amount substantially between about 0.0001-10%, preferably 0.01-1%, by weight of the mixture. Thus, the present invention contemplates overall compositions which comprise mixtures of a conventional dispersible carrier vehicle such as (1) a dispersible inert finely divided carrier solid, and/or (2) a dispersible carrier liquid such as an inert organic solvent and/or water, preferably including a surface-active effective amount of a carrier vehicle assistant, e.g., a surface-active agent, such as an emulsifying agent and/or a dispersing agent, and an amount of the active compound which is effective for the purpose in question and which is generally between about 0.0001-95%, and preferably 0.01-95%, by weight of the mixture.

The active compounds can also be used in accordance with the well known ultra-low-volume process with good success, i.e., by applying such compound if normally a liquid, or by applying a liquid composition containing the same, via very effective atomizing equipment, in finely divided form, e.g., average particle diameter of from 50-100 microns, or even less, i.e., mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g., about 20-100% by weight of the active compound.

Furthermore, the present invention contemplates methods of selectively killing, combating or controlling pests, e.g., insects, which comprises applying to at least one of correspondingly (a) such insects, and (b) the corresponding habitat thereof, i.e., the locus to be protected, e.g., to a growing crop, to an area where a crop is to be grown or to a domestic animal, a correspondingly combative or toxic amount, i.e., an insecticidally effective amount, of the particular active compound of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, dressing, encrusting, and the like.

It will be realized, of course, that the concentration of the particular active compound utilized in admixture with the carrier vehicle will depend upon the intended application. Therefore, in special cases it is possible to go above or below the aforementioned concentration ranges.

The unexpected superiority and outstanding activity of the particular new compounds of the present invention are illustrated, without limitation, by the following examples:

EXAMPLE 1

Drosophila Test

Solvent: 3 parts by weight of acetone
Emulsifier: 1 part by weight of alkylaryl polyglycol ether To produce a suitable preparation of active compound, 1 part by weight of the active compound was mixed with the stated amount of solvent containing the stated amount of emulsifier, and the concentrate was diluted with water to the desired concentration.

1 cm$^3$ of the preparation of the active compound was applied with a pipette to a filter paper disc of 7 cm diameter. The wet disc was placed over the orifice of a glass vessel containing 50 vinegar flies (*Drosophila melanogaster*) and covered with a glass plate.

After the specified periods of time, the destruction was determined in %. 100% means that all the flies were killed; 0% means that no flies were killed.

The active compounds, the concentrations of the active compounds, the evaluation times and the results can be seen from the following Table 1.

EXAMPLE 2

Plutella Test

Solvent: 3 parts by weight of acetone
Emulsifier: 1 part by weight of alkylaryl polyglycol ether To produce a suitable preparation of active compound, 1 part by weight of the active compound was Table 1

| Active compound | (Drosophila test) Active compound concentration in % | Degree of destruction in % after 1 day |
|---|---|---|
| (known) (B) — 6-methoxybenzothiophen-3-yl O,O-diethyl phosphorothioate | 0.1 | 0 |
| (2) — benzofuran, O-P(=S)(SC₃H₇-n)(OC₂H₅), 2-CO-OC₃H₇-iso | 0.1 | 100 |
| (1) — 5-Cl-benzofuran, O-P(=S)(SC₃H₇-n)(OC₂H₅), 2-CO-OC₂H₅ | 0.1 | 100 |
| (9) — 5-Cl-benzofuran, O-P(=S)(SC₃H₇-n)(OC₂H₅), 2-CO-OC₃H₇-iso | 0.1 | 100 |
| (10) — 5,7-diCl-benzofuran, O-P(=S)(SC₃H₇-n)(OC₂H₅), 2-CO-OC₃H₇-iso | 0.1 | 100 |
| (6) — 6-CH₃-benzofuran, O-P(=S)(SC₃H₇-n)(OC₂H₅), 2-CO-OC₂H₅ | 0.1 | 100 |
| (5) — 7-OCH₃-benzofuran, O-P(=S)(SC₃H₇-n)(OC₂H₅), 2-CO-OC₂H₅ | 0.1 | 100 | mixed with the stated amount of solvent containing the stated amount of emulsifier and the concentrate was diluted with water to the desired concentration.

Cabbage leaves (*Brassica oleracea*) were sprayed with the preparation of the active compound until dew moist and were then infested with caterpillars of the diamond-back moth (*Plutella maculipennis*).

After the specified periods of time, the degree of destruction was determined as a percentage: 100% means that all the caterpillars were killed whereas 0% means that none of the caterpillars were killed.

The active compounds, the concentrations of the active compounds, the evaluation times and the results can be seen from the following Table 2:

Table 2
(*Plutella* test)

| Active compound | Active compound concentration in % | Degree of destruction in % after 3 days |
|---|---|---|
| (known) (B) — benzothiophene with CH$_3$O, O—P(=S)(C$_2$H$_5$)$_2$ | 0.1 <br> 0.01 | 100 <br> 0 |
| (known) (A) — benzothiophene with CH$_3$O, O—P(=S)(OC$_2$H$_5$)$_2$ | 0.1 <br> 0.01 | 100 <br> 0 |
| (2) — benzofuran, O—P(=S)(OC$_2$H$_5$)(SC$_3$H$_7$-n), 2-CO—OC$_3$H$_7$-iso | 0.1 <br> 0.01 | 100 <br> 100 |
| (1) — 5-Cl-benzofuran, O—P(=S)(OC$_2$H$_5$)(SC$_3$H$_7$-n), 2-CO—OC$_2$H$_5$ | 0.1 <br> 0.01 | 100 <br> 100 |
| (9) — 5-Cl-benzofuran, O—P(=S)(OC$_2$H$_5$)(SC$_3$H$_7$-n), 2-CO—OC$_3$H$_7$-iso | 0.1 <br> 0.01 | 100 <br> 100 |
| (10) — 5,7-diCl-benzofuran, O—P(=S)(OC$_2$H$_5$)(SC$_3$H$_7$-n), 2-CO—OC$_3$H$_7$-iso | 0.1 <br> 0.01 | 100 <br> 100 |
| (6) — 6-CH$_3$-benzofuran, O—P(=S)(OC$_2$H$_5$)(SC$_3$H$_7$-n), 2-CO—OC$_2$H$_5$ | 0.1 <br> 0.01 | 100 <br> 100 |

Table 2-continued
(Plutella test)

| Active compound | Active compound concentration in % | Degree of destruction in % after 3 days |
|---|---|---|
| (5) | 0.1<br>0.01 | 100<br>100 |
| (4) | 0.1<br>0.01 | 100<br>100 |

The following further examples are set forth to illustrate, without limitation, the manner of producing the instant compounds according to the present invention:

EXAMPLE 3 a. The 2-carbalkoxy-3-hydroxybenzofuran derivatives (III) used as starting materials were prepared for example as described below:

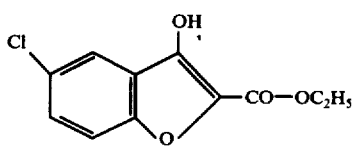
(IIIa)

12.3 g (0.11 mol) of potassium tert.-butylate were added in portions to a solution of 28.6 g (0.1 mol) of (2-carbethoxy-4-chlorophenoxy)-acetic acid ethyl ester in 50 ml of ethanol. The batch was warmed to 80°C for 2 hours and was then cooled, and the reaction mixture was poured into 200 ml of water. The aqueous solution was first extracted with methylene chloride (to remove neutral impurities) and was then acidified with hydrochloric acid while cooling with ice. The acid solution was repeatedly extracted with methylene chloride. The combined organic extracts were dried over sodium sulfate and then concentrated. 21 g (87.5% of theory) of 2-carbethoxy-5-chloro-3-hydroxy-benzofuran were obtained in the form of colorless crystals of melting point 100°–102°C.

The following compounds of the formula

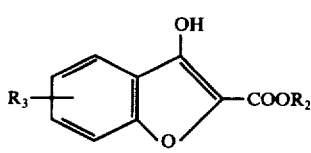

were prepared analogously:

| | R2 | R3 | Yield (% of theory) | Physical data (melting point, °C) |
|---|---|---|---|---|
| (IIIb) | —C₃H₇—iso | H | 62 | 79-82 |
| (IIIc) | —C₃H₇—iso | 5-Cl | 55 | 106-108 |

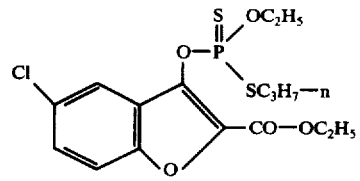
(1)

21.4 g (0.1 mol) of O-ethyl-S-n-propyl-thionothiolphosphoric acid diester chloride were added dropwise at 20° C to a mixture of 24.0 g (0.1 mol) of 2-carbethoxy-5-chloro-3-hydroxybenzofuran, 14.5 g (0.105 mol) of potassium carbonate and 200 ml of acetonitrile. The reaction mixture was allowed to continue reacting for 3 hours at 40° C and was then cooled, and 300 ml of toluene were added. The toluene solution was washed with saturated sodium bicarbonate solution and water, dried over sodium sulfate and then concentrated. After slight distillation, 31 g (73% of theory) of O-ethyl-S-n-propyl-O-[2-carbethoxy-5-chloro-benzofuran(3)yl]-thionothiolphosphoric acid ester were obtained in the form of a brown oil of refractive index $n_D^{24}$: 1.5641.

The following compounds of the formula

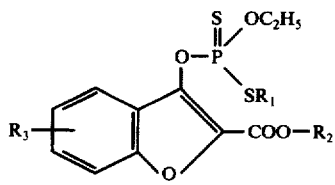

were prepared analogously:

| Compound No. | R2 | R3 | R1 | Yield (% of theory) | Physical data (refractive index) |
|---|---|---|---|---|---|
| 2 | -C₃H₇-iso | H | -C₃H₇-n | 67 | $n_D^{21}$:1.5442 |
| 3 | -C₃H₇-n | 5-Cl | -C₃H₇-n | 77 | $n_D^{21}$:1.5659 |
| 4 | -C₃H₇-iso | H | -C₄H₉-n | 79 | $n_D^{21}$:1.5585 |

EXAMPLE 4

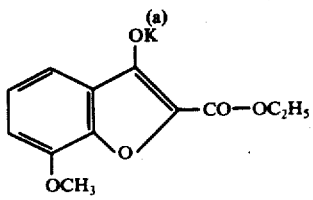

(a)

12.3 g (0.11 mol) of potassium tert.-butylate were added in portions to a solution of 28.2 g (0.1 mol) of (2-carbethoxy-6-methoxyphenoxy)-acetic acid ethyl ester in 30 ml of ethanol. The mixture was warmed to 80° C for 2 hours and was then cooled, and 150 ml of acetonitrile were added dropwise to the crystal sludge. The precipitate was then filtered off and dried. 21 g (77% of theory) of the potassium salt of 2-carbethoxy-3-hydroxy-7-methoxy-benzofuran were obtained in the form of gray crystals of melting point 200° C.

The compounds of the following formula

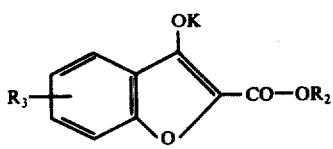

were synthesized analogously:

| | R2 | R3 | Yield (% of theory) | Physical data, (melting point, °C) |
|---|---|---|---|---|
| (IIIe) | -C₂H₅ | 6-CH3 | 73 | 200 |
| (IIIf) | -C₃H₇-iso | 5,7-dichloro | 84 | 265 |

(b)

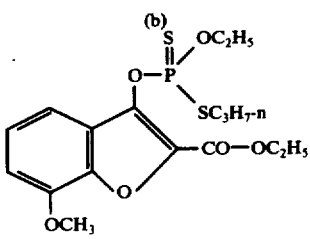

(5)

21.4 g (0.1 mol) of O-ethyl-S-n-propyl-thionothiolphosphoric acid diester chloride were added dropwise at 20° C to a suspension of 27.4 g (0.1 mol) of the potassium salt of 2-carbethoxy-3-hydroxy-7-methoxy-benzofuran in 200 ml of acetonitrile. The batch was allowed to continue reacting for 4 hours at 40° C and was then cooled, and the reaction mixture was poured into 300 ml of toluene. The toluene solution was washed with saturated sodium bicarbonate solution and water, dried over sodium sulfate and concentrated. After slight distillation, 29.0 g (69.5% of theory) of O-ethyl-S-n-propyl-O-[2-carbethoxy-7-methoxy-benzofuran(3)yl]-thionothiolphosphoric acid ester were obtained in the form of a yellow oil of refractive index $n_D^{26}$: 1.5610.

The following compounds of the formula

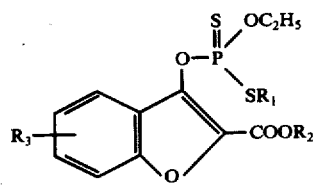

(IIId)

were prepared analogously:

| Compound No. | R2 | R3 | R1 | Yield (% of theory) | Physical data (refractive index) |
|---|---|---|---|---|---|
| 6 | -C₂H5 | 6-CH3 | -C₃H₇-n | 79.5 | $n_D^{26}$:1.5595 |
| 7 | -C₃H₇-n | 5,7-dichloro | -C₃H₇-n | 78 | $n_D^{21}$:1.5716 |
| 8 | -C₃H₇-n | 5,7-dichloro | -C₄H₉-n | 84 | $n_D^{21}$:1.5445 |

Other compounds of formula (I) which can be similarly prepared include:

| Compound No. | R | R1 | R2 | R3 | n |
|---|---|---|---|---|---|
| 9 | -C₂H5 | -C₃H₇-n | -C₃H₇-iso | 5-Cl | 1 |
| 10 | -C₂H5 | -C₃H₇-n | -C₃H₇-iso | 5,7-diCl | 2 |
| 11 | -C₃H₇-n | -C₄H₉-sec | -C₂H5 | 5,6-diCl | 2 |
| 12 | -CH3 | -CH3 | -CH3 | 5-Cl, 7-OC₂H5 | 2 |
| 13 | -C₄H₉-sec | -C₅H₁₁-n | -C₄H₉-sec | 4-C₂H5 | 1 |

It will be appreciated that the instant specification and examples are set forth by way of illustration and not limitation, and that various modifications and changes may be made without departing from the spirit and scope of the present invention.

What is claimed is:

1. An O-alkyl-S-alkyl-O-[2-carbalkoxy-benzofuran(3-)yl]-thionothiolphosphoric acid ester of the formula

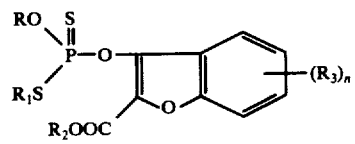

(I)

in which
R, R₁ and R₂ each independently is alkyl with 1 to 6 carbon atoms,
R₃ is halogen, or alkyl or alkoxy with 1 to 4 carbon atoms, and
n is an integer from 0 to 4.

2. An ester according to claim 1 in which R is alkyl with 1 to 3 carbon atoms, R₁ is alkyl with 1 to 5 carbon atoms, R₂ is alkyl with 1 to 4 carbon atoms, R₃ is chlorine, methoxy, ethoxy, methyl or ethyl, and n is 0, 1 or 2.

3. A compound according to claim 1, wherein such compound is O-ethyl-S-n-propyl-O-[2-carbethoxy-5- chloro-benzofuran-(3)yl]-thionothiolphosphoric acid ester of the formula

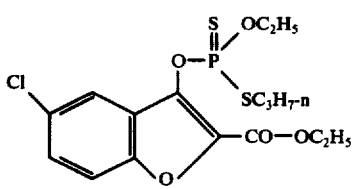

4. A compound according to claim 1, wherein such compound is O-ethyl-S-n-propyl-O-[2-carbisopropoxy-benzofuran(3)yl]-thionothiolphosphoric acid ester of the formula

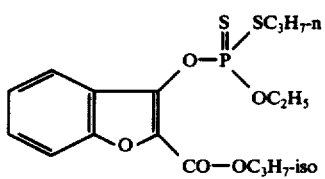

5. A compound according to claim 1, wherein such compound is O-ethyl-S-n-propyl-O-[2-carbopropoxy-5-chloro-benzofuran(3)yl]-thionothiolphosphoric acid ester of the formula

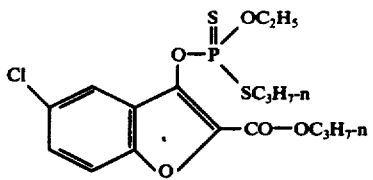

6. A compound according to claim 1, wherein such compound is O-ethyl-S-n-propyl-O-[2-carbethoxy-7-methoxy-benzofuran(3)yl]-thionothiolphosphoric acid ester of the formula

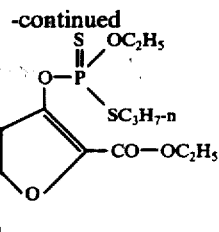

7. A compound according to claim 1, wherein such compound is O-ethyl-S-n-propyl-O-[2-carbopropoxy-5,7-dichloro-benzofuran(3)yl]-thionothiolphosphoric acid ester of the formula

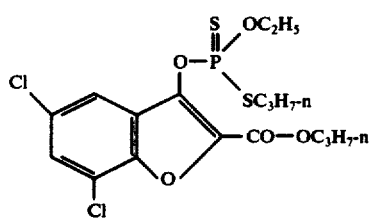

8. An insecticidal composition containing as active ingredient an insecticidally effective amount of a compound according to claim 1 in admixture with a diluent.

9. A method of combating insect pests which comprises applying to the pests or a habitat thereof an insecticidally effective amount of a compound according to claim 1.

10. The method according to claim 9 in which said compound is

O-ethyl-S-n-propyl-O-[2-carbethoxy-5-chloro-benzofuran-(3)yl]-thionothiolphosphoric acid ester, O-ethyl-S-n-propyl-O-[2-carbisopropoxy-benzofuran(3)yl]-thionothiolphosphoric acid ester, O-ethyl-S-n-propyl-O-[2-carbopropoxy-5-chloro-benzofuran(3)yl]-thionothiolphosphoric acid ester, O-ethyl-S-n-propyl-O-[2-carbethoxy-7-methoxy-benzofuran(3)yl]-thionothiolphosphoric acid ester, or O-ethyl-S-n-propyl-O-[2-carbopropoxy-5,7-dichloro-benzofuran(3)yl]-thionothiolphosphoric acid ester.

* * * * *